United States Patent
Pi et al.

(10) Patent No.: US 10,349,848 B2
(45) Date of Patent: Jul. 16, 2019

(54) CONVERSION CIRCUIT AND DETECTION CIRCUIT

(71) Applicant: SHENZHEN GOODIX TECHNOLOGY CO., LTD., Shenzhen, Guangdong (CN)

(72) Inventors: Tao Pi, Guangdong (CN); Mengwen Zhang, Guangdong (CN); Chang Zhan, Guangdong (CN)

(73) Assignee: SHENZHEN GOODIX TECHNOLOGY CO., LTD., Shenzhen (CN)

( * ) Notice: Subject to any disclaimer, the term of this patent is extended or adjusted under 35 U.S.C. 154(b) by 169 days.

(21) Appl. No.: 15/693,555

(22) Filed: Sep. 1, 2017

(65) Prior Publication Data

US 2017/0360315 A1    Dec. 21, 2017

Related U.S. Application Data (63) Continuation of application No. PCT/CN2016/090468, filed on Jul. 19, 2016.

(30) Foreign Application Priority Data

Dec. 29, 2015    (CN) .......................... 2015 1 1016745

(51) Int. Cl.
     *H02M 11/00*      (2006.01)
     *A61B 5/024*      (2006.01)
     (Continued)

(52) U.S. Cl.
     CPC ........ *A61B 5/02427* (2013.01); *G11C 27/026* (2013.01); *H03F 1/086* (2013.01);
     (Continued)

(58) Field of Classification Search
     CPC ..................................................... H02M 11/00
     (Continued)

(56) References Cited

U.S. PATENT DOCUMENTS

| | | | |
|---|---|---|---|
| 5,644,385 A | 7/1997 | Mizuno | |
| 7,242,174 B1 * | 7/2007 | Sheu ...................... | B82Y 10/00 |
| | | | 324/76.11 |

(Continued)

FOREIGN PATENT DOCUMENTS

| | | |
|---|---|---|
| CN | 101106360 A | 1/2008 |
| CN | 101221068 A | 7/2008 |

(Continued)

OTHER PUBLICATIONS

Chinese Office Action issued by the State Intellectual Property Office of the Peoples' Republic of China, dated Feb. 26, 2019.

(Continued)

*Primary Examiner* — Hai L Nguyen
(74) *Attorney, Agent, or Firm* — Heslin Rothenberg Farley & Mesiti P.C.

(57) ABSTRACT

A conversion circuit for converting a current signal into a first output voltage signal, where the current signal flows through a sensing component, is provided. The conversion circuit includes: a first current eliminating circuit, configured to eliminate a first current in the current signal. The first current eliminating circuit includes: a current sample and hold circuit; and a current driving circuit, coupled between the sensing component and the current sample and hold circuit; a second current eliminating circuit, coupled to the sensing component and configured to eliminate a second current in the current signal; and an integrating circuit, coupled to the sensing component and configured to integrate a third current in the current signal, and output a first (Continued)

input voltage signal between a first integration output terminal and a second integration output terminal.

19 Claims, 6 Drawing Sheets

(51) Int. Cl.
    *H03F 1/26*     (2006.01)
    *G11C 27/02*     (2006.01)
    *H03F 3/45*     (2006.01)
    *H03F 1/08*     (2006.01)
    *H03F 3/00*     (2006.01)
    *H03F 3/08*     (2006.01)
    *H03F 3/30*     (2006.01)
    *H03M 1/46*     (2006.01)

(52) U.S. Cl.
    CPC ............... *H03F 1/26* (2013.01); *H03F 3/005* (2013.01); *H03F 3/082* (2013.01); *H03F 3/3022* (2013.01); *H03F 3/45475* (2013.01); *H03M 1/468* (2013.01); *A61B 2562/0238* (2013.01); *H03F 2200/249* (2013.01); *H03F 2200/264* (2013.01); *H03F 2200/297* (2013.01); *H03F 2200/372* (2013.01); *H03F 2200/375* (2013.01); *H03F 2200/462* (2013.01)

(58) Field of Classification Search
    USPC ........................................................ 327/103
    See application file for complete search history.

(56) References Cited

U.S. PATENT DOCUMENTS

| 8,248,111 | B2* | 8/2012 | Kitsunezuka | G11C 27/02 |
| | | | | 327/103 |
| 8,692,200 | B2 | 4/2014 | Tao et al. | |
| 9,576,679 | B2* | 2/2017 | Powell | G11C 27/026 |
| 9,712,254 | B2* | 7/2017 | Noda | H04B 10/272 |
| 2008/0007344 | A1 | 1/2008 | Natzke | |
| 2009/0167422 | A1 | 7/2009 | Edwards et al. | |
| 2010/0065720 | A1 | 3/2010 | Raynor et al. | |
| 2010/0114211 | A1 | 5/2010 | Donofrio et al. | |
| 2010/0158055 | A1 | 6/2010 | Giebel | |
| 2015/0011851 | A1 | 1/2015 | Mehta et al. | |

FOREIGN PATENT DOCUMENTS

| CN | 101470139 A | 7/2009 |
| CN | 101806619 A | 8/2010 |
| CN | 202553925 U | 11/2012 |

OTHER PUBLICATIONS

International Search Report issued in PCT/CN2016/090468, dated Oct. 20, 2016.

Extended European Search Report for European Patent Application No. 16880555 dated Apr. 3, 2018.

\* cited by examiner

CONVERSION CIRCUIT AND DETECTION CIRCUIT

CROSS-REFERENCE TO RELATED APPLICATIONS

The present application is a continuation application of PCT application No. PCT/CN2016/090468 submitted on Jul. 19, 2016, which is based upon and claims priority to Chinese patent application No. 201511016745.8 on Dec. 29, 2015, both of which are incorporated herein for reference in their entireties.

TECHNICAL FIELD

The present patent application relates to the field of electronic technologies, and in particular, relates to a conversion circuit and a detection circuit which are capable of eliminating a photoelectric current.

BACKGROUND

With the development of science and technology, heartbeat detection function is employed in wearable electronic devices, which makes a light-emitting diode (LED) irradiate towards inner of a human body. The light penetrating through or reflected from the human body is sensed by using a photodiode or a phototransistor, and an optical signal (that is, a photoelectric current) sensed by the photodiode or phototransistor is converted into a voltage signal by using a heartbeat detection circuit.

An existing heartbeat detection circuit converts the photoelectric current flowing through the photodiode or the phototransistor into a voltage signal by using a transimpedance amplifier (TIA, which is also referred to as a current-to-voltage converter). However, the heartbeat signal has a very small amplitude, and is easy to be impacted by background light from the environment. The transimpedance amplifier is incapable of eliminating a background photoelectric current, and thus accuracy of judgment of the heartbeat signal is affected. Further, the transimpedance amplifier has a high power consumption, and is easy to be impact by noise. Therefore, an improvement to the existing heartbeat detection circuit is desired.

SUMMARY

A first technical problem to be solved by some embodiments of the present invention is to provide a conversion circuit to eliminate the impacts caused by a background photoelectric current.

An embodiment of the present invention provides a conversion circuit for converting a current signal into a first output voltage signal where the current signal flows through a sensing component. The conversion circuit includes:
a first current eliminating circuit, configured to eliminate a first current in the current signal, the first current eliminating circuit including:
 a current sample and hold circuit; and
 a current driving circuit, coupled between the sensing component and the current sample and hold circuit;
a second current eliminating circuit, coupled to the sensing component and configured to eliminate a second current in the current signal; and
an integrating circuit, coupled to the sensing component and configured to integrating for a third current in the current signal, the integrating circuit having a first integration output terminal and a second integration output terminal, wherein the first integration output terminal and the second integration output terminal are configured to output the first output voltage signal.

A second technical problem to be solved by some embodiments of the present invention is to provide a detection circuit. The detection circuit includes:
a photodiode, configured to receive a reflected light and generate a current signal according to the reflected light; and
a conversion circuit as described above;
a fully differential amplification circuit, including:
 a first input terminal, coupled to a first integration output terminal of the conversion circuit;
 a second input terminal, coupled to a second integration output terminal of the conversion circuit;
 a first output terminal; and
 a second output terminal.

In the conversion circuit according to some embodiments of the present invention, a background photoelectric current and a base current in the current signal may be eliminated, and integration may be carried out for a heartbeat current in the current signal by using the integrating circuit, such that the impacts caused by the background photoelectric current and the base current to the heartbeat current are removed, and the detection efficiency is improved.

DETAILED DESCRIPTION

In order to make the objectives, technical solutions, and advantages of the present invention clearer, the present invention is further described in detail below by reference to some exemplary embodiments and the accompanying drawings. It should be understood that the embodiments described here are only some exemplary ones for illustrating the present invention, and are not intended to limit the present invention.

Figure 1:
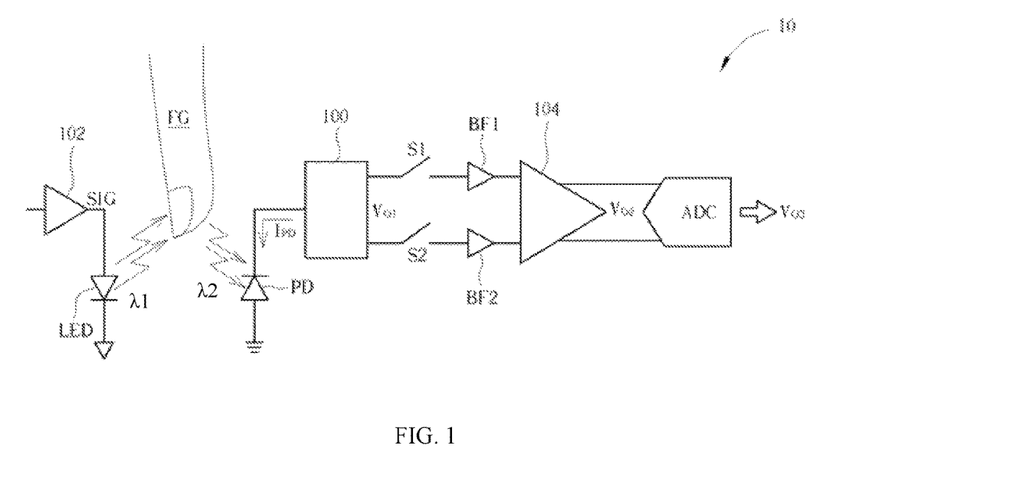
FIG. 1 is a schematic diagram of a detection circuit according to an embodiment of the present invention.

Referring to FIG. 1, FIG. 1 is a schematic diagram of a detection circuit 10 according to an embodiment of the present invention. The detection circuit 10 may be configured to detect a heartbeat of a human body, and the detection circuit 10 includes a driving circuit 102, a light-emitting diode LED, a photodiode PD, a conversion circuit 100, a fully differential amplification circuit 104 and an analog-to-digital converter ADC.

The driving circuit 102 is coupled to the light-emitting diode LED, and configured to generate a base signal SIG to drive the light-emitting diode LED. The light-emitting diode LED generates an incident light λ1 according to the base signal SIG. The incident light λ1 irradiates a particular part of the human body, for example, a finger FG, such that the finger FG generates a reflected light λ2. The photodiode PD is configured to receive the reflected light λ2 and generate a current signal $I_{PD}$ according to the reflected light λ2. The conversion circuit 100 is coupled to the photodiode PD, and configured to convert the current signal $I_{PD}$ into an output voltage $V_{O1}$ and output an output voltage $V_{O1}$ to the fully differential amplification circuit 104. The fully differential amplification circuit 104 amplifies the output voltage $V_{O1}$ to a voltage $V_{O2}$ and outputs the voltage $V_{O2}$ to the analog-to-digital converter ADC. The analog-to-digital converter ADC converts the analog voltage $V_{O2}$ into a digital signal $V_{O3}$, and output the digital signal $V_{O3}$ to a rear end operation circuit for subsequent operation and processing.

In an embodiment, the detection circuit 10 may include switches S1 and S2 and buffers BF1 and BF2. The switches S1 and S3 and the buffers BF1 and BF2 are coupled between the conversion circuit 100 and the fully differential amplification circuit 104. For example, the switch S1 and the buffer BF1 are serially connected between a first output terminal of the conversion circuit 100 and a first input terminal of the fully differential amplification circuit 104; the switches 2 and the buffer BF2 are serially connected to a second output terminal of the conversion circuit and a second input terminal of the fully differential amplification circuit 104.

It should be noted that the incident light λ1 generated by the light-emitting diode LED is a modulated light, a heartbeat signal of a human body is modulated on the base signal SIG to generate the reflected light λ2, and the photodiode PD generates the current signal $I_{PD}$ according to the reflected light λ2. Therefore, the current signal $I_{PD}$ includes a background photoelectric current $I_{BG}$, a base current $I_{SIG}$ and a heartbeat current $I_{HB}$ (that is, $I_{PD}=I_{BG}+I_{SIG}+I_{HB}$). The background photoelectric current $I_{BG}$ is a current from background light of the environment and caused by the photodiode PD. The base current $I_{SIG}$ is a modulated base current relevant to the base signal SIG. The heartbeat current $I_{HB}$ is a useful signal indicating the heartbeat of the human body. The heartbeat current $I_{HB}$ is very small relative to the background photoelectric current $I_{BG}$ and the base current $I_{SIG}$. In this case, the conversion circuit 100 may extract the heartbeat current $I_{HB}$ from the current signal $I_{PD}$, that is, differentiating the heartbeat current $I_{HB}$ from the background photoelectric current $I_{BG}$ and the base current $I_{SIG}$. In other words, the conversion circuit 100 may eliminate the background photoelectric current $I_{BG}$ and the base current $I_{SIG}$ of the current signal $I_{PD}$, and carry out integration for the heartbeat current $I_{HB}$ of the current signal $I_{PD}$. As such, the output voltage $V_{O1}$ actually indicates the heartbeat of the human body.

Figure 2:
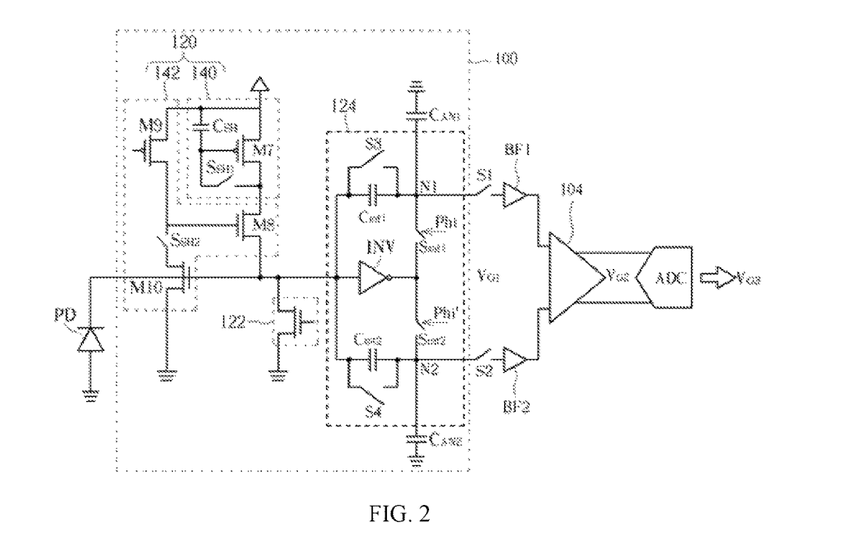
FIG. 2 is a schematic diagram of a conversion circuit according to an embodiment of the present invention.

Specifically, referring to FIG. 2, FIG. 2 is a schematic diagram of a conversion circuit 100 according to an embodiment of the present invention. The conversion circuit 100 includes a current eliminating circuit 120 (corresponding to a first current eliminating circuit), a current eliminating circuit 122 (corresponding to a second current eliminating circuit), noise suppression capacitors $CAN_1$ (corresponding to a first noise suppression capacitor) and $C_{AN2}$ (corresponding to a second noise suppression capacitor) and an integrating circuit 124. The current eliminating circuit 120, the current eliminating circuit 122 and the integrating circuit 124 are all coupled to a photodiode PD. The current eliminating circuit 120 is configured to eliminate a background photoelectric current $I_{BG}$ (corresponding to a first current) of a current signal $I_{PD}$. The current eliminating circuit 122 is configured to eliminate a base current $I_{SIG}$ (corresponding to a second current) of the current signal $I_{PD}$. The integrating circuit 124 is configured to carry out integration for a heartbeat current $I_{HB}$ (corresponding to a third current) in the current signal $I_{PD}$, generate an output voltage $V_{O1}$ (corresponding to a first output voltage), and output the output voltage $V_{O1}$ to a node between integration output terminals N1 and N2 of the integrating circuit 124. The detection circuit 10 transfers the output voltage $V_{O1}$ to the fully differential amplification circuit 104 via switches S1, S2 and buffers BF1, BF2. In addition, the noise suppression capacitors $CAN_1$ and $C_{AN2}$ are respectively coupled to the integration output terminals N1 and N2, and configured to reduce a bandwidth of the entire conversion circuit 100, and thus reduce noise energy between the integration output terminals N1 and N2 to achieve the effect of noise suppression.

In detail, the integrating circuit 124 includes an inverting amplifier INV, integrating capacitors $C_{int1}$, $C_{int2}$, integrating switches $S_{int1}$, $S_{int2}$, switches S3 and S4. The inverting amplifier INV has an input terminal and an output terminal. As illustrated in FIG. 2, the integrating capacitor $C_{int1}$ is coupled between the input terminal of the inverting amplifier INV and the integration output terminal N1, and the integrating capacitor $C_{int2}$ is coupled between the input terminal of the inverting amplifier INV and the integration output terminal N2. The switch S3 is coupled between the input terminal of the inverting amplifier INV and the integration output terminal N1, and the switch S4 is coupled between the input terminal of the inverting amplifier INV and the integration output terminal N2. The integrating switch $S_{int1}$ is coupled between the integration output terminal N1 and the output terminal of the inverting amplifier INV, and the integrating switch $S_{int2}$ is coupled between the integration output terminal N2 and the output terminal of the inverting amplifier INV. The integrating switches $S_{int1}$ and $S_{int2}$ are respectively controlled by signals Phi and Phi'; the signals Phi and Phi' are frequency signals that are not overlapped with each other. In this case, during a first duration, the integrating switch $S_{int1}$ is switched off and the integrating switch $S_{int2}$ is switched on, the integrating circuit 124 carries out integration for the heartbeat current $I_{HB}$ of the current signal $I_{PD}$ by using the integrating capacitor $C_{int1}$, and the noise suppression capacitor $CAN_1$ suppresses the noise of the integrating capacitor $C_{int1}$. During a second duration, the integrating circuit $S_{int2}$ is switched off and the integrating circuit $S_{int1}$ is switched on, the integrating circuit 134 carries out integration for the heartbeat current $I_{HB}$ of the current signal $I_{PD}$ by using the integrating capacitor $C_{int2}$, and the noise suppression capacitor $C_{AN2}$ suppresses the noise of the integrating capacitor $C_{int2}$.

It should be noted that with increasing of the integration duration, the voltage difference (that is, the output voltage $V_{O1}$) between the integration output terminals N1 and N2 may be increased. In addition, the noise suppression capacitors $C_{AN1}$ and $C_{AN2}$ are respectively coupled to the integration output terminals N1 and N2, and the noise suppression capacitors $C_{AN1}$ and $C_{AN2}$ may not generate an excessive step response, whereas power consumption of the inverting amplifier INV can be reduced. Therefore, the detection circuit 10 achieves reduction of power consumption and noise by using the noise suppression capacitors $C_{AN1}$ and $C_{AN2}$ coupled to the integration output terminals N1 and N2.

In addition, the current eliminating circuit 122 may be practiced using an N-type field effect transistor, and the current eliminating circuit 122 may be controlled by the signal Phi'. In other words, the current eliminating circuit 122 may generate, during the second duration, a current to eliminate the base current $I_{SIG}$ of the current signal $I_{PD}$.

The current eliminating circuit 120 includes a current sample and hold circuit 140 and a current driving circuit 142. The current sample and hold circuit 140 includes a transistor M7, a sample and hold capacitor $C_{SH}$, and a sample and hold switch $S_{SH1}$. The transistor M7 may be a P-type field effect transistor, the sample and hold capacitor $C_{SH}$ is coupled between a source and a gate of the transistor M7, and the sample and hold switch $S_{SH1}$ is coupled between the gate and a drain of the transistor M7. The current driving circuit 142 is coupled between the current sample and hold circuit 140 and the photodiode PD, and the current driving circuit 142 includes transistors M8, M9, M10 and a sample and hold switch $S_{SH2}$. The transistor M9 may be a P-type field effect transistor, and the transistors M8 and M10 may be N-type field effect transistors. The transistor M9 is coupled between the source of the transistor M7 and a gate of the transistor M8, a drain of the transistor M8 is coupled to the drain of the transistor M7, and a source of the transistor M8 and a gate of the transistor M10 are both coupled to the photodiode PD. One terminal of the sample and hold switch $S_{SH2}$ is coupled to the gate of the transistor M8 and a drain of the transistor M9, and the other terminal of the sample and hold switch $S_{SH2}$ is coupled to a drain of the transistor M10. When the sample and hold switches $S_SH1$ and $S_{SH2}$ are both switched off, the current eliminating circuit 120 rapidly generates a current to eliminate the background photoelectric current $I_{BG}$ of the current signal $I_{PD}$. In conclusion, the current eliminating circuit 120 is a rapid current sample and hold circuit, which, in addition to eliminating the background photoelectric current $I_{BG}$ of the current signal $I_{PD}$, further rapidly charges an equivalent capacitor inside the photodiode PD, to shorten the initialization time required by the conversion circuit 100, and hence to reduce power consumption.

Accordingly, the conversion circuit 100 eliminates the background photoelectric current $I_{BG}$ of the current signal $I_{PD}$ by using the current eliminating circuit 120, eliminates the base current $I_{SIG}$ of the current signal $I_{PD}$ by using the current eliminating circuit 122, and carries out integration for the heartbeat current $I_{HB}$ of the current signal $I_{PD}$ by using the integrating circuit 124, to thereby improve the detection efficiency. Further, the conversion circuit 100 suppresses the noise by using the noise suppression capacitors $C_{AN1}$ and $C_{AN2}$ coupled to the integration output terminals N1 and N2, thereby achieving reduction of power consumption and noise.

Figure 3:
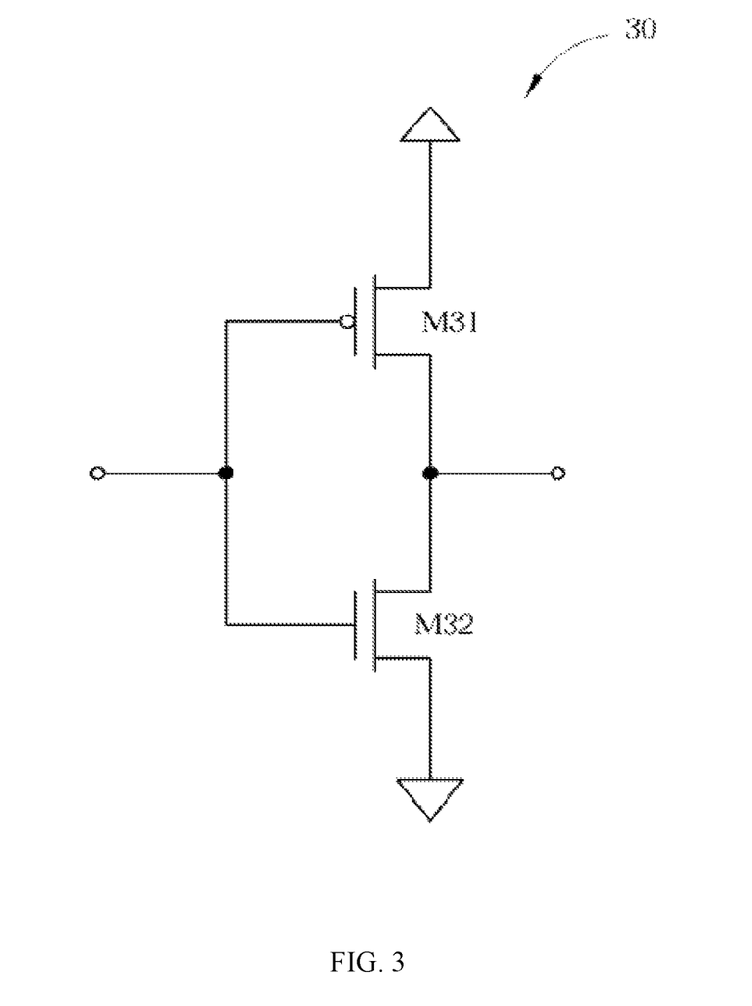
FIG. 3 is a schematic diagram of one inverting amplifier in FIG. 2 according to an embodiment of the present invention.

It should be noted that the preceding embodiments are used to describe the concepts of some embodiments of the present invention. A person skilled in the art may make different modifications to the present invention without any limitation to the above given embodiments. For example, practice of the inverting amplifier INV in the integrating circuit 124 is not limited to a specific architecture. For example, referring to FIG. 3, FIG. 3 is a schematic diagram of an inverting amplifier 30. The inverting amplifier 30 may be used to practice the inverting amplifier INV, and the inverting amplifier 30 includes transistors M31 and M32; the transistor M31 is a P-type field effect transistor and the transistor M32 is an N-type field effect transistor. A gate and a drain of the transistor M31 are respectively coupled to a gate and a drain of the transistor M32, the gates of the transistor 31 and transistor M32 form an input terminal of the inverting amplifier 30, and the drains of the transistor M31 and transistor M32 form an output terminal of the inverting amplifier 30.

Figure 4:
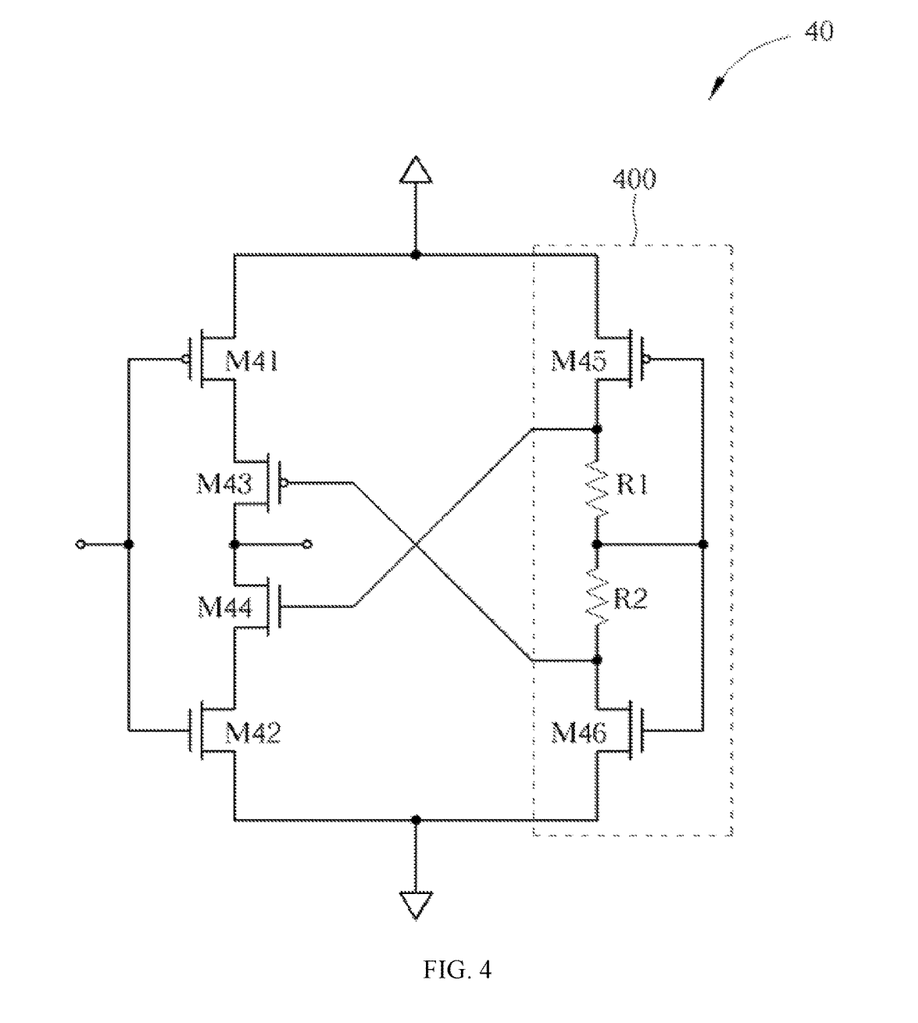
FIG. 4 is a schematic diagram of another inverting amplifier in FIG. 2 according to an embodiment of the present invention.

In another aspect, referring to FIG. 4, FIG. 4 is a schematic diagram of another inverting amplifier 40 according to an embodiment of the present invention. The inverting amplifier 40 may be used to practice the inverting amplifier INV, and the inverting amplifier 40 includes transistors M41 to M44 and a bias circuit 400. The bias circuit 400 includes transistors M45, M46 and resistors R1, R2. The transistors M41, M43 and M45 are all P-type field effect transistors, and the transistors M42, M44 and M46 are all N-type field effect transistors.

As illustrated in FIG. 4, a gate of the transistor M41 is coupled to a gate of the transistor M42 to form an input terminal of the inverting amplifier 40, and a drain of the transistor M43 is coupled to a drain of the transistor M44 to form an output terminal of the inverting amplifier 40. A drain of the transistor M41 is coupled to a source of the transistor M43, a drain of the transistor M42 is coupled to a source of the transistor M44, a gate of the transistor M43 is coupled to a drain of the transistor M46, a gate of the transistor M44 is coupled to a drain of the transistor M45, a gate of the transistor M45 is coupled to a gate of the transistor M46; the resistor R1 is coupled between the gate of the transistor M45 and the drain of the transistor M45, and the resistor R2 is coupled between the gate of the transistor M46 and the drain of the transistor M46.

It should be noted that the transistors M41, M42 and the transistors M43, M44 collaboratively form a cascade structure, which further improves a direct current gain of the inverting amplifier, and thus reduces a coupling degree of signals between the first duration and the second duration, and improves a linearity and signal-to-noise ratio of the integrating circuit 124. In another aspect, the transistors M45 and M46 in the bias circuit 400 are respectively in a mirror relationship with the transistors M41 and M42 therein. When voltages of the transistors M41 to M44 change, voltage of the bias circuit 400 varies adaptively. In other words, the bias circuit 400 can increase a dynamic range of the inverting amplifier 40. In addition, the resistors R1 and R2 may pull down a gate voltage of the transistor M43 and pull up a gate voltage of the transistor M44, to prevent the transistors M41 and M42 from entering a linear region.

Figure 5:
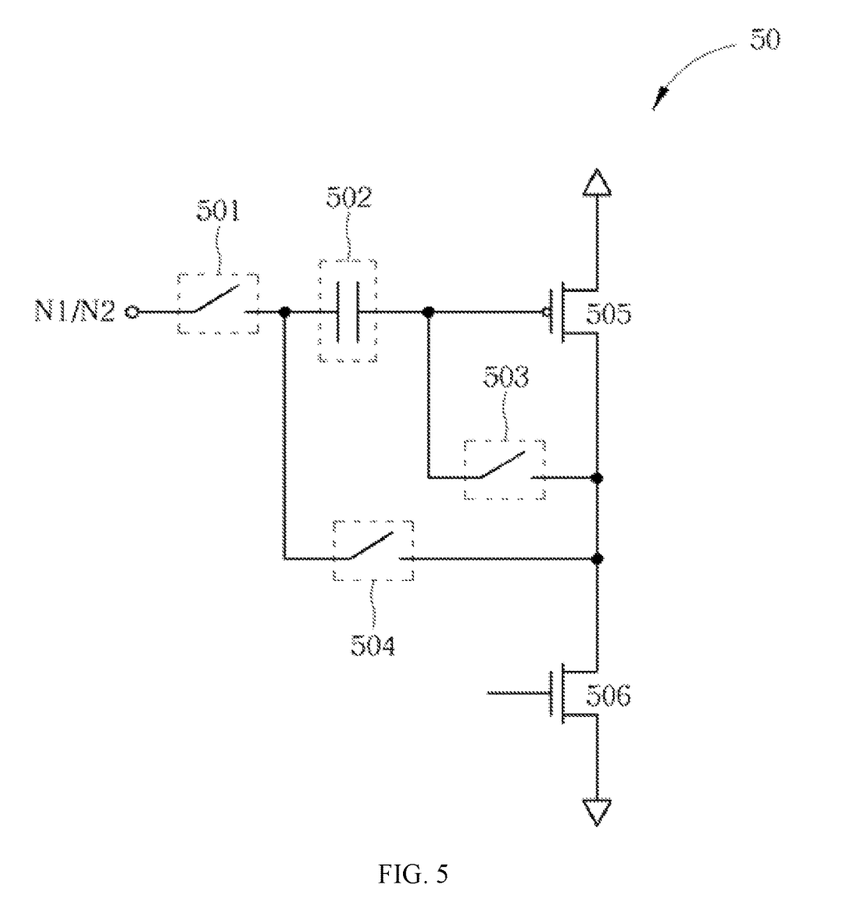
FIG. 5 is a schematic diagram of a buffer in FIG. 1 according to an embodiment of the present invention.

In addition, practice of the buffers BF1 and BF2 is not limited to a specific architecture. For example, referring to FIG. 5, FIG. 5 is a schematic diagram of a buffer 50 according to an embodiment of the present invention. The buffer 50 may be used to practice any one of the buffers BF1 and BF2. The buffer 50 includes switches 501, 503, 504, a capacitor 502 and transistors 505, 506. During a third duration, the switches 501 and 503 are switched off and the switch 504 is switched on, and the capacitor 502 samples the output voltage of the integrating circuit 124; during a fourth duration, the switch 504 is switched off and the switches 501 and 503 are switched on, and the buffer 50 holds the output voltage of the integrating circuit 124, and outputs the output voltage to the fully differential amplification circuit 104.

Figure 6:
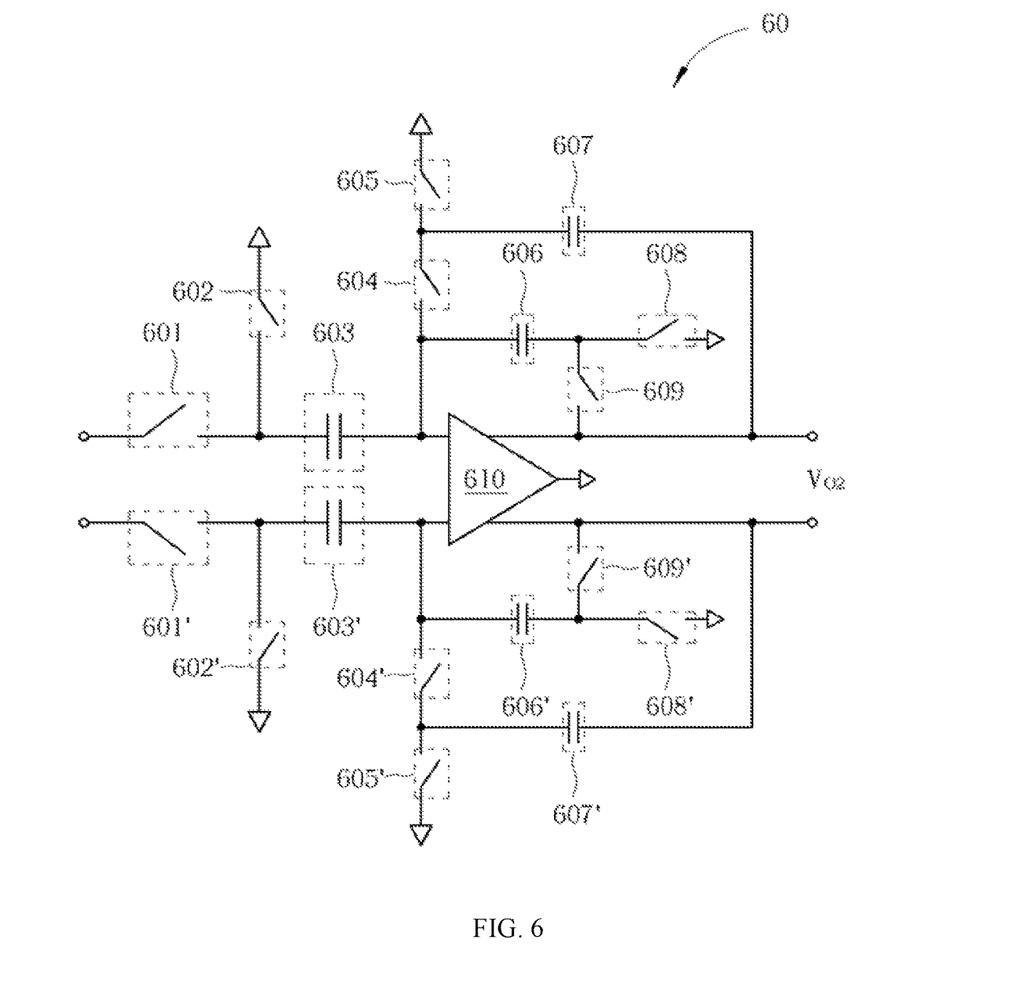
FIG. 6 is a schematic diagram of a fully differential amplification circuit in FIG. 1 according to an embodiment of the present invention.

In addition, practice of the fully differential amplification circuit 104 is not limited to a specific architecture. For example, referring to FIG. 6, FIG. 6 is a schematic diagram of a fully differential amplification circuit 60 according to an embodiment of the present invention. The fully differential amplification circuit 60 may be used to practice the fully differential amplification circuit 104. The fully differential amplification circuit 60 includes a fully differential operational amplifier 610, capacitors 603, 606, 607, 603', 606' and 607', and switches 601, 602, 604, 605, 608, 609, 601', 602', 604', 605', 608' and 609'. The switches 602, 605, 609, 602', 605' and 609' are controlled by the signal Phi, and the switches 601, 604, 608, 601', 604' and 608' are controlled by the signal Phi'. During the second duration, the switches 601, 604, 608, 601', 604' and 608' are switched off and the switches 602, 605, 609, 602', 605' and 609' are switched on, and the capacitors 603 and 603' sample the output voltages of the buffers BF1 and BF2; and during the first duration, the switches 602, 605, 609, 602', 605' and 609' are switched off and the switches 601, 604, 608, 601', 604' and 608' are switched on, and the fully differential amplification circuit 104 transfers the charges stored in the capacitors 603 and 603' to the capacitors 606 and 606'. By controlling the switches using the signals Phi and Phi', the circuit architecture of the fully differential amplification circuit 60 can fully eliminate impacts caused by an offset voltage, a limited gain and flicker noise, and thus enhances the efficiency of the fully differential amplification circuit.

Figure 7:
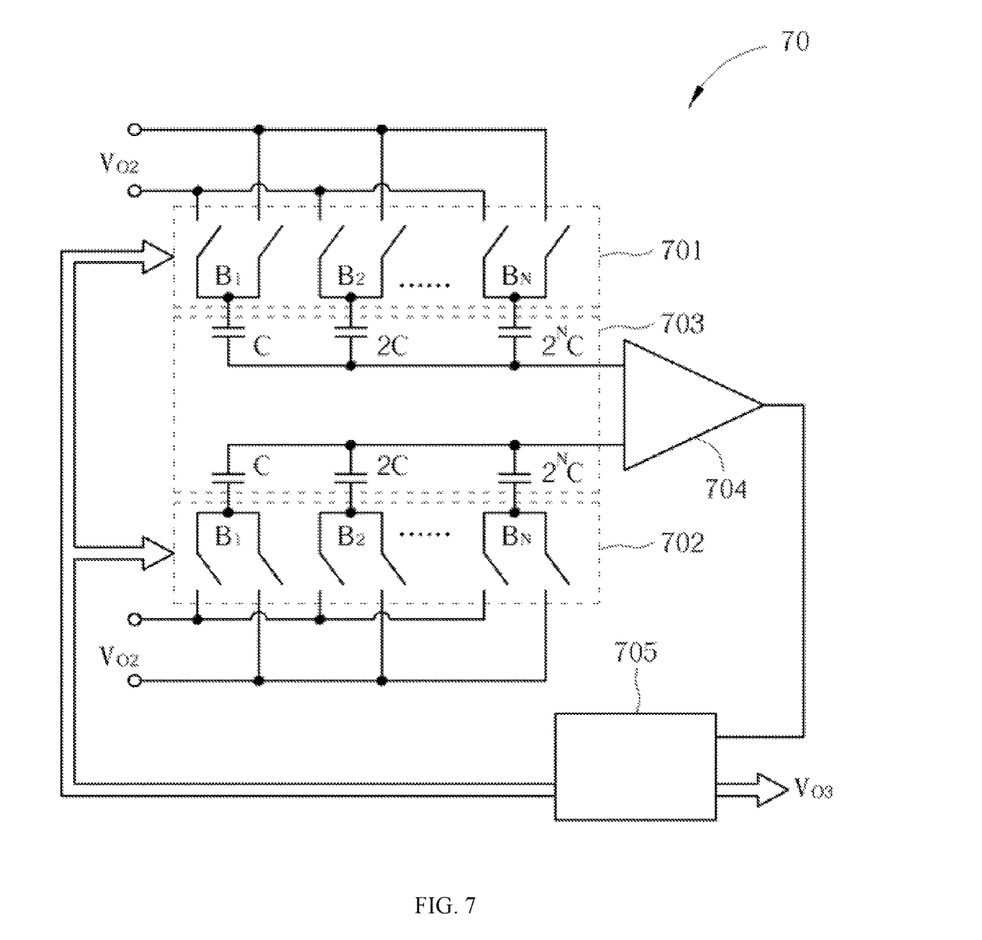
FIG. 7 is a schematic diagram of an analog-to-digital converter in FIG. 1 according to an embodiment of the present invention.

In addition, practice of the analog-to-digital converter ADC is not limited to a specific architecture. For example, referring to FIG. 7, FIG. 7 is a schematic diagram of an analog-to-digital converter 70. The analog-to-digital converter 70 may be used to practice the analog-to-digital converter ADC. The analog-to-digital converter 70 includes a first correlation array 701, a second correlation array 702, a capacitor array 703, a comparator 704 and a logic module 705. The first correlation array 701 and the second correlation array 702 both includes switches B1 to BN, and the first correlation array 701 and the second correlation array 702 are both coupled to the capacitor array 703. The capacitor array 703 includes capacitors C, 2C to $2^N$C. The logic module 705 controls conduction of the switches B1 to BN of the first correlation array 701 and the second correlation array 702 according to an output comparison result of the comparator 704, and converts an analog voltage $V_{O2}$ into a digital voltage $V_{O3}$. The other operation details of the analog-to-digital converter 70 are well known by a person skilled in the art, which is thus not described herein any further.

In conclusion, in the conversion circuit according to some embodiments of the present invention, a background photoelectric current and a base current in the current signal may be eliminated, and integration may be carried out for a heartbeat current in the current signal by using the integrating circuit, such that the impacts caused by the background photoelectric current and the base current to the heartbeat current are removed, and the detection efficiency is improved. Further, the conversion circuit further suppresses the noise by a noise suppression capacitor, thereby achieving reduction of power consumption and noise.

Described above are merely some preferred embodiments of the present invention, but are not intended to limit the present invention. Any modification, equivalent replacement, or improvement made without departing from the spirit and principle of the present invention should fall within the protection scope of the present invention.

What is claimed is:

1. A conversion circuit for converting a current signal flowing through a sensing component into a first output voltage signal, comprising:
a first current eliminating circuit configured to eliminate a first current in the current signal, the first current eliminating circuit comprising:
a current sample and hold circuit; and
a current driving circuit coupled between the sensing component and the current sample and hold circuit;
a second current eliminating circuit coupled to the sensing component and configured to eliminate a second current in the current signal; and
an integrating circuit coupled to the sensing component and configured to integrate a third current in the current signal, the integrating circuit having a first integration output terminal and a second integration output terminal, wherein the first integration output terminal and the second integration output terminal are configured to output the first output voltage signal.

2. The conversion circuit according to claim 1, wherein the integrating circuit comprises:
an inverting amplifier comprising an input terminal and an output terminal;
a first integrating capacitor coupled between the input terminal of the inverting amplifier and the first integration output terminal; and
a second integrating capacitor coupled between the input terminal of the inverting amplifier and the second integration output terminal.

3. The conversion circuit according to claim 2, wherein the integrating circuit further comprises:
a first integrating switch coupled between the output terminal of the inverting amplifier and the first integration output terminal; and
a second integrating switch, coupled between the output terminal of the inverting amplifier and the second integration output terminal.

4. The conversion circuit according to claim 2, wherein the inverting amplifier comprises:
a first transistor comprising a first terminal, a second terminal and a third terminal; and
a second transistor comprising:
a first terminal electrically connected to the first terminal of the first transistor;
a second terminal coupled to the second terminal of the first transistor; and
a third terminal;
wherein the first terminal of the first transistor and the first terminal of the second transistor are input terminals of the inverting amplifier.

5. The conversion circuit according to claim 4, wherein the second terminal of the first transistor and the second terminal of the second transistor are output terminals of the inverting amplifier.

6. The conversion circuit according to claim 4, wherein the inverting amplifier further comprises:
a third transistor comprising:
a first terminal;
a second terminal; and
a third terminal coupled to the second terminal of the first transistor; and
a fourth transistor, comprising:
a first terminal;
a second terminal coupled to the second terminal of the third transistor; and
a third terminal coupled to the second terminal of the second transistor.

7. The conversion circuit according to claim 6, wherein the second terminal of the third transistor and the second terminal of the fourth transistor are output terminals of the inverting amplifier.

8. The conversion circuit according to claim 6, wherein the first terminal of the third transistor and the first terminal of the fourth transistor are coupled to a bias circuit.

9. The conversion circuit according to claim 8, wherein the bias circuit comprises:
   a fifth transistor, comprising:
      a first terminal;
      a second terminal coupled to the first terminal of the fourth transistor; and
      a third terminal;
   a sixth transistor comprising:
      a first terminal coupled to the first terminal of the fifth transistor;
      a second terminal coupled to the first terminal of the third transistor; and
      a third terminal;
   a first resistor coupled between the first terminal of the fifth transistor and the second terminal of the fifth transistor; and
   a second resistor, coupled between the first terminal of the sixth transistor and the second terminal of the sixth transistor.

10. The conversion circuit according to claim 1, wherein the current sample and hold circuit comprises:
   a seventh transistor comprising a first terminal, a second terminal and a third terminal;
   a sample and hold capacitor coupled between the first terminal of the seventh transistor and the third terminal of the seven transistor; and
   a first sample and hold switch coupled between the first terminal of the seventh transistor and the second terminal of the seventh transistor.

11. The conversion circuit according to claim 10, wherein the current driving circuit comprises:
   an eighth transistor, comprising:
      a first terminal;
      a second terminal coupled to the second terminal of the seventh transistor; and
      a third terminal coupled to the sensing component;
   a ninth transistor, comprising:
      a first terminal;
      a second terminal coupled to the first terminal of the eighth transistor; and
      a third terminal;
   a second sample and hold switch coupled to the first terminal of the eighth transistor; and
   a tenth transistor, comprising:
      a first terminal, coupled to the sensing component;
      a second terminal, coupled to the second sample and hold switch; and
      a third terminal.

12. The conversion circuit according to claim 1, wherein the second current eliminating circuit comprises a transistor controlled by a frequency signal.

13. The conversion circuit according to claim 1, wherein the sensing circuit is a sensing diode.

14. The conversion circuit according to claim 1, further comprising:
   a first noise suppression capacitor coupled to the first integration output terminal; and
   a second noise suppression capacitor coupled to the second integration output terminal.

15. A detection circuit, comprising:
   a photodiode configured to receive a reflected light and generate a current signal according to the reflected light;
   a conversion circuit;
   a fully differential amplification circuit, comprising:
      a first input terminal coupled to a first integration output terminal of the conversion circuit;
      a second input terminal coupled to a second integration output terminal of the conversion circuit;
   a first output terminal; and
   a second output terminal;
   wherein the conversion circuit is configured for converting the current signal flowing through a sensing component into a first output voltage signal, comprising:
   a first current eliminating circuit configured to eliminate a first current in the current signal, the first current eliminating circuit comprising:
      a current sample and hold circuit; and
      a current driving circuit coupled between the sensing component and the current sample and hold circuit;
   a second current eliminating circuit coupled to the sensing component and configured to eliminate a second current in the current signal; and
   an integrating circuit coupled to the sensing component and configured to integrate a third current in the current signal, the integrating circuit having a first integration output terminal and a second integration output terminal, wherein the first integration output terminal and the second integration output terminal are configured to output the first output voltage signal.

16. The detection circuit according to claim 15, further comprising an analog-to-digital converter coupled between the first output terminal of the fully differential amplification circuit and the second output terminal of the fully differential amplification circuit.

17. The detection circuit according to claim 15, further comprising:
   a first switch coupled between the first integration output terminal of the conversion circuit and the first input terminal of the fully differential amplification circuit; and
   a second switch, coupled between the second integration output terminal of the conversion circuit and the second input terminal of the fully differential amplification circuit.

18. The detection circuit according to claim 15, further comprising:
   a first buffer coupled between the first integration output terminal of the conversion circuit and the first input terminal of the fully differential amplification circuit; and
   a second buffer coupled between the second integration output terminal of the conversion circuit and the second input terminal of the fully differential amplification circuit.

19. The detection circuit according to claim 15, further comprising:
   a light-emitting diode configured to generate an incident light to a human body, the human body generating the reflected light; and
   a driving circuit coupled to the light-emitting diode.

* * * * *